(12) United States Patent
Dumond et al.

(10) Patent No.: US 7,704,432 B2
(45) Date of Patent: Apr. 27, 2010

(54) IMPRINT LITHOGRAPHIC METHOD FOR MAKING A POLYMERIC STRUCTURE

(75) Inventors: Jarrett Dumond, Singapore (SG); Hong Yee Low, Singapore (SG)

(73) Assignee: Agency for Science, Technology and Research, Singapore (SG)

( * ) Notice: Subject to any disclaimer, the term of this patent is extended or adjusted under 35 U.S.C. 154(b) by 1014 days.

(21) Appl. No.: 11/436,833

(22) Filed: May 18, 2006

(65) Prior Publication Data

US 2006/0214330 A1 Sep. 28, 2006

Related U.S. Application Data

(63) Continuation-in-part of application No. 10/852,448, filed on May 24, 2004.

(51) Int. Cl.
- *B28B 3/06* (2006.01)
- *A61M 25/00* (2006.01)
- *B29C 59/02* (2006.01)
- *B28B 7/10* (2006.01)

(52) U.S. Cl. .................. 264/297.4; 264/264; 264/320; 264/334

(58) Field of Classification Search ............ 264/320, 264/334, 264, 297.4
See application file for complete search history.

(56) References Cited

U.S. PATENT DOCUMENTS

| | | | |
|---|---|---|---|
| 4,705,659 A | 11/1987 | Bernstein et al. | 264/29.6 |
| 4,943,750 A | 7/1990 | Howe et al. | 310/309 |
| 5,654,220 A | 8/1997 | Leedy | 438/25 |
| 5,943,574 A | 8/1999 | Tehrani et al. | 438/300 |
| 6,111,356 A | 8/2000 | Roitman et al. | 313/506 |
| 6,297,516 B1 | 10/2001 | Forrest et al. | 257/40 |
| 2003/0096446 A1 | 5/2003 | Lim et al. | 438/99 |
| 2003/0217804 A1 | 11/2003 | Guo et al. | 156/230 |

(Continued)

FOREIGN PATENT DOCUMENTS

EP 0592094 B1 4/1994

(Continued)

OTHER PUBLICATIONS

USPTO Office Action dated Jul. 25, 2008 for U.S. Appl. No. 11/089,101.

(Continued)

*Primary Examiner*—Monica A Huson
*Assistant Examiner*—Michael T Piery
(74) *Attorney, Agent, or Firm*—Winstead P.C.

(57) ABSTRACT

An imprint lithographic method for making a polymeric structure comprising the steps of:
- (a) providing a mold having a shape forming a mold pattern;
- (b) providing a substrate having a higher surface energy relative to said mold;
- (c) providing a polymer film on said mold, said polymer film having a selected thickness, wherein the selected thickness of the polymer film on the mold pattern is capable of forming at least one frangible region in the polymer film having a thickness that is less than the remainder of the polymer film;
- (d) pressing the mold and the substrate relatively toward each other to form said frangible region; and
- (e) releasing at least one of said mold and said substrate from the other, wherein after said releasing, said frangible region remains substantially attached to said mold while the remainder of said polymer film forms the polymeric structure attached to said substrate.

33 Claims, 12 Drawing Sheets

U.S. PATENT DOCUMENTS

2004/0150590 A1 8/2004 Cok et al.
2004/0231781 A1* 11/2004 Bao et al. .................. 156/230

FOREIGN PATENT DOCUMENTS

| EP | 0732868 A1 | 9/1996 |
|---|---|---|
| EP | 0767599 A2 | 4/1997 |
| EP | 1003221 A2 | 5/2000 |
| EP | 1324081 A2 | 7/2003 |
| WO | WO 02/21883 A1 | 3/2002 |
| WO | WO 02/064354 A1 | 8/2002 |
| WO | WO 03/065474 A1 | 8/2003 |

OTHER PUBLICATIONS

Andrew et al., "Photonic band structure and emission characteristics of a metal-backed polymeric distributed feedback laser," *Appl. Phys. Lett.*, 81:954-956 (2002).

Cumpston et al., "Two-photon polymerization initiators for three-dimensional optical data storage and microfabrication," *Nature*, 398:51-54 (1999).

Bao et al., "Nanoimprinting over topography and multilayer three-dimensional printing," *J. Vac. Sci. Technol. B*, 20:2881-2886 (2002).

Brittain et al., "Microorigami: Fabrication of Small Three-Dimensional Metallic Structures," *J. Phys. Chem. B*, 105:347-350 (2001).

Chen et al., "A non-destructive method for the removal of residual resist in imprinted patterns," *Microelectronic Engineering*, 67-68:245-251 (2003).

Huang et al., "Reversal imprinting by transferring polymer from mold to substrate," *J. Vac. Sci. Technol. B*, 20(6):2872-2876 (2002).

Huck et al., "Three-Dimensional Mesoscale Self-Assembly," *J. Am. Chem. Soc.*, 129:8267-8268 (1998).

Kiriakidis et al., "Fabrication of 2-D and 3-D Photonic Band-Gap Crystal in the GHz and THz Region," *Mater. Phys. Mech.*, 1:20-26 (2000).

Li et al., "Direct three-dimensional patterning using nanoimprint lithography," *App. Phys. Lett.*, 78(21):3322-3324 (2001).

Moran et al., "Novel technologies for the realisation of GaAs pHEMTs with 120 nm self-aligned and nanoimprinted T-gates," *Microelectronic Engineering*, 67-68:769-774 (2003).

Stehr et al., "A low threshold polymer laser based on metallic nanoparticle gratings," *Adv. Mater.*, 15:1726-1729 (2003).

Sun et al., "Multilayer resist methods for nanoimprint lithography on nonflat surfaces," *J. Vac. Sci. Technol. B*, 16(6):3922-3925 (1998).

Tabata et al., "3D Fabrication by Moving Mask Deep X-ray Lithography with Multiple Stages," The Fifteenth IEEE International Conference on Micro Electro Mechanical Systems, 180-183 (2002).

Zaumseil et al., "Three-Dimensional and Multilayer Nanostructures Formed by Nanotransfer Printing," *Nano Lett.*, 3:1223-1227 (2003).

* cited by examiner

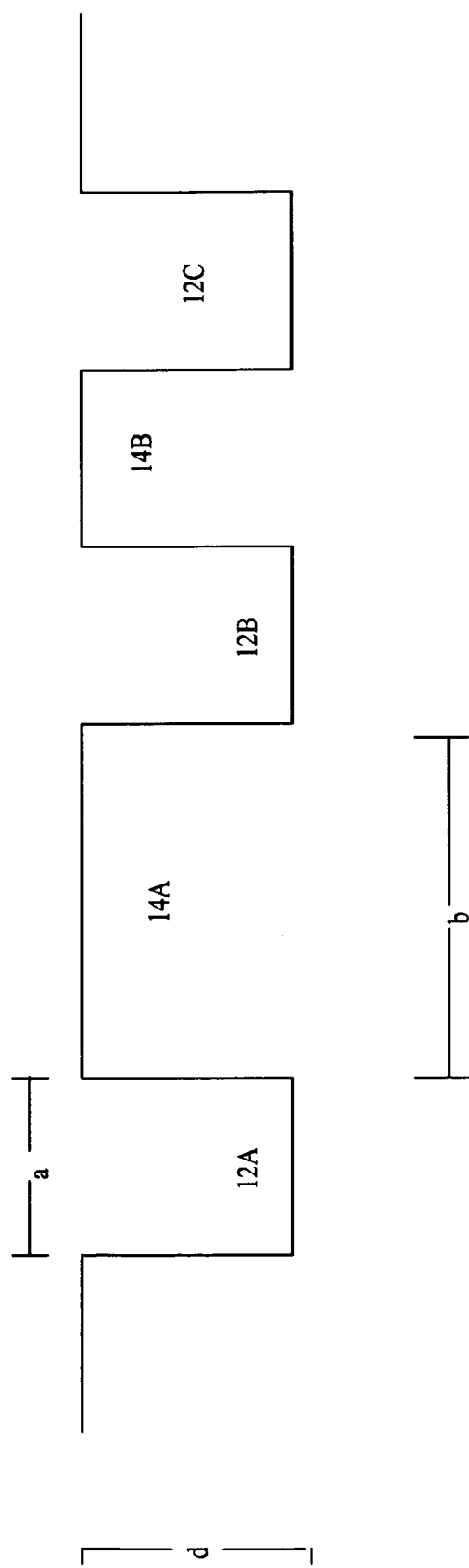

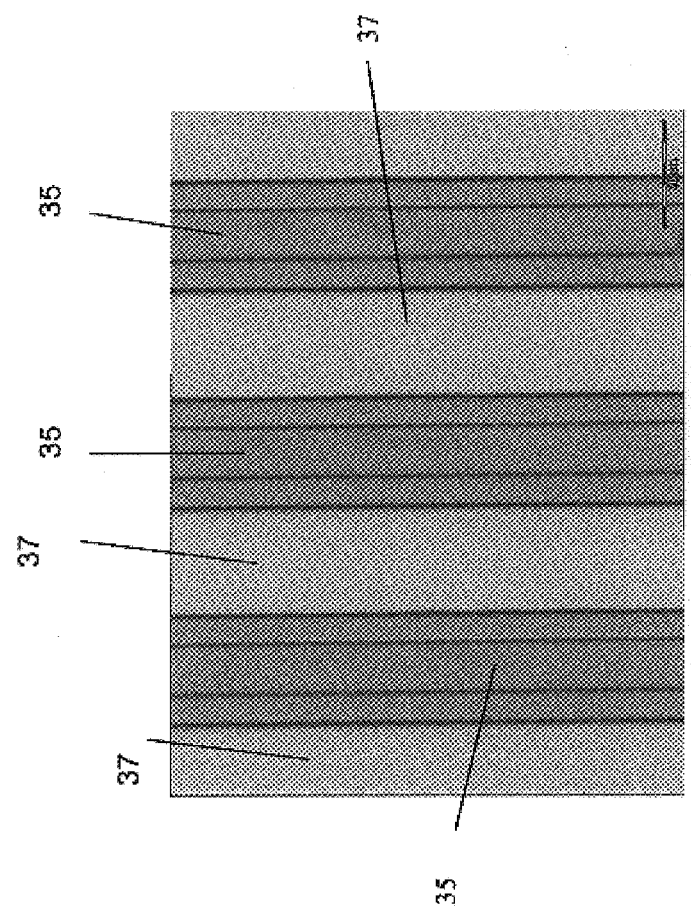

IMPRINT LITHOGRAPHIC METHOD FOR MAKING A POLYMERIC STRUCTURE

TECHNICAL FIELD

The present invention relates in general to an imprint lithographic method for making a polymeric structure and in particular, a micro-sized or nano-sized polymeric structure.

BACKGROUND

Conventional photolithography is believed to be limited to about 150 nm in pattern dimensions. While X-ray and ion beam lithography have been demonstrated as viable alternative techniques for creating pattern dimensions below this limit, they are expensive. E-beam lithography has also been proven as a viable technique. However, it is time consuming and, like X-ray and ion beam lithography, expensive. In contrast to such lithographic techniques, imprinting offers an attractive alternative to the fabrication of two-dimensional (2-D) nanometer-scale features, as a result of simpler, faster, and cheaper processing, making this technique a potential replacement for photolithography in mass production.

The above-mentioned lithographic techniques are further limited to fabrication of 2-D and supported features. Imprinting, however, can lend itself to the fabrication of three-dimensional (3-D) features, wherein 3-D features comprise structural variation with depth. Three-dimensional patterning techniques are likely to be important enabling technologies for a number of applications. In microelectronics, for example, the third dimension could possibly allow the speed and memory of microprocessors to go beyond the limitations currently imposed by 2-D features. In optoelectronic industries, 3-D photonic band gap structures are garnering considerable attention because 3-D structures serve to minimize loss of light [Kiriakidis et al., "Fabrication of 2-D and 3-D Photonic Band-Gap Crystal in the GHz and THz Region," *Mater. Phys. Mech.*, 1:20-26, 2000]. In drug/chemical delivery systems, sensing systems and catalysis, the feasibility of fabricating 3-D structures will provide breakthroughs in the efficiency of controlled delivery, sensing, and selectivity in chemical reactions. For example, a sphere with a meshed surface can be envisioned as a chambered pill that contains multiple drugs or a multifunctional catalysis support.

While 2-D fabrication techniques are mature technology down to the sub-micrometer scale, very little has been reported regarding 3-D sub-micrometer fabrication techniques. Currently, of the limited amount of literature available on sub-micrometer 3-D fabrication techniques, most reports are seen to be mere extensions of various photolithography techniques. For instance, Whitesides et al. have shown that a porous microsphere can be obtained via a self-assembly approach [Huck et al., "Three-Dimensional Mesoscale Self-Assembly," *J. Am. Chem. Soc.*, 129:8267-8268, 1998], and Yamamoto et al. have demonstrated the fabrication of micrometer scale grooved structures using deep X-ray lithography [Tabata et al., "3D Fabrication by Moving Mask Deep X-ray Lithography with Multiple Stages," The Fifteenth IEEE International Conference on Micro Electro Mechanical Systems, 180-183, 2002]. Whitesides et al. have also reported on a "membrane folding" method used to create 3-D structures [Brittain et al., "Microorigami: Fabrication of Small Three-Dimensional Metallic Structures," *J. Phys. Chem. B*, 105:347-350, 2001]. While most of these techniques have demonstrated the feasibility of creating 3-D sub-micrometer or nanometer scale features, they are not easily implemented for mass production.

Both conventional nano-imprinting [Sun et al., "Multilayer resist methods for nanoimprint lithography on nonflat surfaces," *J. Vac. Sci. Technol. B*, 16(6):3922-3925, 1998] and reversal imprinting [Huang et al., "Reversal imprinting by transferring polymer from mold to substrate," *J. Vac. Sci. Technol. B*, 20(6):2872-2876, 2002] techniques are attractive alternatives to the above-mentioned techniques in the fabrication of 3-D nano-features, although currently both techniques create 3-D structures through multiple imprinting on patterned substrates or on substrates with topology.

In a known nanoimprint lithography (NIL) process, a thin layer of imprint resist (thermal plastic polymer) is spun coated onto a sample substrate. A mold having predefined topological patterns is brought into contact with the sample and pressed into the polymer coating under certain pressure and at a temperature above the glass transition temperature of the polymer to allow the pattern on the mold to be pressed into the melt polymer film. After being cooled down, the mold is separated from the sample and the pattern resist is left on the substrate. A pattern transfer process, such as reactive ion etching (RIE) is used to transfer the pattern in the resist to the underneath substrate by removal of residue from the substrate.

One known RIE utilizes a gas-plasma to remove the pattern resist from the substrate. A significant disadvantage with this technique is that unless an inorganic mask layer is used to shield the final structures from exposure, the plasma will attack all polymer surfaces, not just the residue layer. This makes adequate preservation of the final structures a difficult task. For example, if the residue layer is too thick, it is necessary to implement a lengthy plasma etch time in order to remove the residue layer. In cases where an inorganic mask layer cannot be used, the dry etching can damage or destroy the final polymer structures. At the very least it would be expected that isotropic etching causes the sidewalls of the final structures to be sloped or tapered rather than vertical.

Additionally, it is known that gas-plasma exposure to most polymeric materials results in chemically modified surfaces, in particular, reactive oxygen plasma often oxidizes the polymer surface. This can be highly undesirable in cases where preservation of the chemical functionality of the polymer structure is important.

Furthermore, depending on the length of the exposure, the physical etching component of an oxygen-plasma RIE etch will roughen the top surface of the final imprinted structures. For most applications, this effect is undesirable. It should be noted that wet-etching has been shown to remove the residue layer, thus avoiding the roughening effect of dry etching, but it is also not selective for the residue layer, which is a prerequisite for this process.

There is a need to provide an imprint lithographic method of making a polymeric structure, particularly three dimensional micro-sized and nano-sized polymeric structures, that overcome or at least ameliorate one or more of the disadvantages described above.

SUMMARY

According to a first aspect of the invention, there is provided an imprint lithographic method for making a polymeric structure comprising the steps of:

(a) providing a mold having a shape forming a mold pattern;

(b) providing a substrate having a higher surface energy relative to said mold;

(c) providing a polymer film on said mold, said polymer film having a selected thickness, wherein the selected thickness of the polymer film on the mold pattern is capable of forming at least one frangible region in the polymer film having a thickness that is less than the remainder of the polymer film;

(d) pressing the mold and the substrate relatively toward each other to form said frangible region; and (e) releasing at least one of said mold and said substrate from the other, wherein after said releasing, said frangible region remains substantially attached to said mold while the remainder of said polymer film forms the polymeric structure attached to said substrate.

Advantageously, breakage of said frangible region avoids the need for a residue-removing step, such as reactive ion etching, from said formed polymeric structure.

In one embodiment, there is provided a method of making a three-dimensional (3-D) polymeric structure comprising the steps of:

(a) forming a polymer film having a selected thickness on a structured surface of a first mold, said polymer film having a first side in contact with said structured surface, a second side opposite to said first side, and a glass transition temperature Tg;

(b) pressing, at a temperature above $T_g$, the second side of the polymer film and a structured surface of a second mold relatively toward each other to form a 3-D structured polymer film therebetween and wherein said selected thickness of said polymer film forms at least one frangible portion thereon, said structured surfaces of the first and second molds having dissimilar surface energies to each other;

(c) separating one of the first or second molds from the polymer film, at a temperature below $T_g$, to attach the 3-D structured polymer film to the mold having a higher surface energy relative to the other mold;

(d) pressing said attached 3-D structured polymer film and a substrate relatively toward each other to attach said 3-D structured polymer film to said substrate, said substrate having a higher surface energy relative to the surface energy of the structured surface; and (e) separating said mold from said 3-D structured polymer film, wherein after said separating, said at least one frangible portion remains substantially attached to said mold while the remainder of said polymer film remains substantially attached to said substrate to form a 3-D polymeric structure thereon.

In a second aspect, there is provided a polymeric structure made in a method according to the first aspect.

DEFINITIONS

The following words and terms used herein shall have the meaning indicated:

The term "Micro-structures" as used herein, refers to structures comprising "micro-scale" features; micro-scale features being defined herein as features having dimensions that range in length from about 1 micrometer (μm) to about 100 μm.

The term "Nano-structures" as used herein, are structures comprising "nano-scale" or "sub-micron" features; nano-scale features being defined herein as features having dimensions below about 1 μm.

The term "relatively toward each other" means, in the context of this specification, the pressing of a mold toward a substrate, or the pressing of a substrate toward a mold, or the pressing of a mold and a substrate toward each other, or the pressing of one mold against another mold or the pressing of two molds against each other.

The terms "Three-dimensional" and abbreviated form "3-D" as used herein, refer to structures or structural features that have both lateral variations (thickness) as well as variations with depth.

The term "Surface energy" as used herein, is a surface characteristic associated with the molecular forces of a particular surface. This surface is generally characterized or quantified as a free surface in contact with the ambient atmosphere. Surface energy is generally measured as $mJ/m^2$ The term "Differential surface energy" as used herein refers to dissimilar surface energies between two or more materials. For the methods described herein, "low surface energy" generally means <12 $mJ/m^2$, "medium surface energy" generally means about 14-30 $mJ/m^2$, and "high surface energy" generally means >50 $mJ/m^2$.

The term "duo-mold" process as used herein, refers to processes wherein two molds, generally with different surface coatings to impart different surface energies, are used to fabricate polymeric 3-D micro- and/or nano-structured objects.

The term "Spin-coating" as used herein generally refers to a process wherein a polymer solution is dispersed on a surface (e.g., a mold) and the surface is rapidly spun centrifugally forcing the solution to spread out and forming a thin layer of de-solvated polymer in the process.

The term "Glass-transition temperature" and abbreviated form "$T_g$" as defined herein, is defined as the temperature at which polymer chains become mobile and begin to slide against each other. Generally, it is the temperature at which the polymer transitions from being generally hard and glassy to a more generally pliable and rubbery state. Above this temperature, such polymers can be induced to flow under pressure. It should be noted that the $T_g$ is not a sharp transition temperature but a gradual transition and is subject to some variation depending on the experimental conditions (e.g., film thickness, tacticity of the polymer, etc.). The actual $T_g$ of a polymer film will vary as a function of film thickness. The $T_g$ will be defined herein as being the bulk glass-transition temperature of the polymer material. The bulk glass transition temperature is a specific value that is widely agreed upon in the literature. For example, the bulk Tg for polymethyl methacrylate (PMMA) is 105° C.

The term "Plasma cleaning" or "plasma treatment" as used herein generally refers to exposure of a surface to a plasma such that organic contaminants on the surface are at least partially destroyed and/or the surface chemistry is changed so that the surface energy is set at a desirable level. Generally such plasma is a low-pressure oxidative plasma such as oxygen ($O_2$), argon, and mixtures of oxygen and argon, generated with a radio frequency (RF) or microwave source. "Plasma etching," as used herein, generally comprises the same principles as plasma cleaning, but is meant to imply the use of a plasma to pattern the surface directly-either through a mask, or by removal of excess material (in the case of a pre-patterned surface).

Unless specified otherwise, the terms "comprising" and "comprise", and grammatical variants thereof, are intended to represent "open" or "inclusive" language such that they include recited elements but also permit inclusion of additional, unrecited elements.

As used herein, the term "about", in the context of concentrations of components of the formulations, typically means +/−5% of the stated value, more typically +/−4% of the stated value, more typically +/−3% of the stated value, more typically, +/−2% of the stated value, even more typically +/−1% of the stated value, and even more typically +/−0.5% of the stated value.

Throughout this disclosure, certain embodiments may be disclosed in a range format. It should be understood that the description in range format is merely for convenience and brevity and should not be construed as an inflexible limitation on the scope of the disclosed ranges. Accordingly, the description of a range should be considered to have specifically disclosed all the possible sub-ranges as well as individual numerical values within that range. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

DISCLOSURE OF EMBODIMENTS

Exemplary, non-limiting embodiments of an imprint lithographic method for making a polymeric structure will now be disclosed. The imprint lithographic method comprises the steps of:

(a) providing a mold having a shape forming a mold pattern;

(b) providing a substrate having a higher surface energy relative to said mold;

(c) providing a polymer film on said mold, said polymer film having a selected thickness, wherein the selected thickness of the polymer film on the mold pattern is capable of forming at least one frangible region in the polymer film having a thickness that is less than the remainder of the polymer film;

(d) pressing the mold and the substrate relatively toward each other to form said frangible region; and (e) releasing at least one of said mold and said substrate from the other, wherein after release, said frangible region remains substantially attached to said mold while the remainder of said polymer film forms the polymeric structure attached to said substrate.

Advantageously, breakage of said frangible region avoids the need for a residue-removing step, such as reactive ion etching, from said formed polymeric structure.

In one disclosed embodiment, the method comprises, before step (a), the step of:

(e) providing first and second molds having respective mold patterns thereon, the surface of said respective mold patterns having dissimilar surface energies.

In one disclosed embodiment, the method comprises, before step (a), the steps of:

(f) forming the polymer film on the first mold, said polymer film having a first side in contact with said mold pattern and a second side opposite to said first side; and (g) pressing, at a temperature above the $T_g$ and at a suitable molding pressure, the second side of the polymer film and the second mold relatively toward each other, wherein said molding pressure is sufficient to form a 3-D structured polymer film between said mold pair.

In one disclosed embodiment, the method comprises, before step (a), the step of:

(h) separating one of the first and second molds from the polymer film, at a temperature below $T_g$, to attach the 3-D structured polymer film to the mold having the higher surface energy relative to the other mold.

In one disclosed embodiment, the method comprises the step of:

(i) detaching said polymeric structure from said substrate.

In one disclosed embodiment, the method comprises the step of:

(j) selecting the thickness of said frangible portion to be 10 nanometers or less.

In one disclosed embodiment, the method comprises the step of:

(k) selecting the thickness of said polymer film to be 1000 nanometers or less.

In one embodiment, said polymeric film has a maximum thickness dimension selected from the range consisting of: about 2000 nanometer to about 100 nanometers.

In one embodiment, the ratio of the maximum thickness of said polymer film relative to the thickness of the frangible region is selected from a ratio range consisting of about 200:1 to about 10:1.

In one embodiment, the method comprises the step of:

(l) spin-coating said polymer onto at least one of said substrate and said mold to form the polymer film thereon.

In one embodiment, said first mold and said second mold patterns are configured to form a polymeric structure therebetween that is substantially T-shaped when viewed in cross-section. In another embodiment, said first mold and said second mold patterns are configured to form, in use, a polymeric structure comprising an array of polymeric bodies that are substantially T-shaped when viewed in cross-section. The T-shaped polymeric bodies comprising a longitudinally shaped strut portion having a longitudinally shaped cross-bar portion at one end thereof, said longitudinally shaped cross-bar portion being disposed at an angle that is substantially normal to the longitudinal axis of said strut portion.

In one embodiment, the cross-bar of said T-shaped structure has at least first and second parts disposed about respective longitudinal axes, wherein said longitudinal axes are not in alignment with each other.

Without being bound by theory, in the T-shaped structure embodiment, during the pressing step the struts of the T-shaped structure may be compressed into the trenches of the mold above the strut. The At least one frangible region may not be similarly compressed because it does not make contact with the substrate. The material within the compressed T-shaped structure moves relative to the material in the frangible regions, thereby leading to a build-up of a shear stress which is sufficiently large enough to break the at least one frangible region from the T-shaped structure. This shear stress build-up occurs along the protrusion edges of the mold. The At least one frangible region can also be sheared off during the releasing step of the mold because the T-shaped structure tends to remain attached to the substrate due to its high surface energy while the at least one frangible region will tend to remain attached to the mold having never made contact with the substrate.

In one embodiment, said first and second mold patterns are configured to provide said frangible portion connecting adjacent cross-bar portions of said array of said T-shaped polymeric bodies.

In one embodiment, said mold pattern is defined in cross-section by at least one recess extending through said mold body, thereby forming protrusions on both sides of the recess.

The selected thickness (t) of said polymer film may be determined according to the following formula (1) for a periodic grating mold:

$$t \approx \frac{d}{(1+b/a)} \quad (1)$$

wherein a is the width of the recess in cross-section, assuming all recesses are geometrically the same;

d is the depth of said recess extending into said mold assuming no variance in depth among the recesses; and b is the width of any particular protrusion in cross-section, assuming all protrusions are geometrically the same.

The temperature and pressure applied during step (e) will be dependent on the polymer used in the polymer film. Generally speaking, the lower the $T_g$ and/or the lower the molecular weight of the polymer, the lower the temperature and pressure limit before deformations are induced in the polymer structures in contact with the substrate. In one embodiment where polymethyl methacrylate (PMMA) having a molecular weight of 15,000 is used, the temperature is held at a temperature below 105° C., more preferably at or below 50° C., before being allowed to cool to room temperature (21° C.). The mold pressure in Step (g), in one exemplary embodiment, is about 50 Bar (5000 kPa) or higher. The mold pressure in one exemplary embodiment is between about 6 Bar (600 kPa) to about 60 Bar (6000 kPa).

The mold may be comprised of any suitable material that is chemically inert to said polymer film and is capable of being surface treated. An exemplary substrate may be comprised of a material selected from the group consisting of silicon, metal, ceramic, polymeric and combinations thereof.

In one embodiment, said the surface of said mold pattern is silane-treated.

In one embodiment, the surface of the mold pattern of said first mold is silane-treated surface of medium energy and the surface pattern of said second mold is a silane-treated surface of low energy.

In some disclosed embodiments, a duo-mold approach is employed in the above-described methods. In some embodiments, surface treatments are employed to impart differential surface energies to different molds and/or different parts of the mold(s). Such surface treatments permit the formation of three-dimensional (3-D) micro- and/or nano-structures through imprinting and the transfer of such structures to a substrate. In some or other embodiments, such surface treatments can facilitate separation of the 3-D structures from the molds to form free-standing micro- and/or nano-structures individually and/or in a film. In some embodiments, such surface treatments can involve silanes, coatings, plasma deposition or treatment, and/or grafting treatments.

In some disclosed embodiments, supported or free-standing stacked 3-D micro- and/or nano-structures are fabricated by using polymers of progressively lower glass transition temperatures or with miscible polymer blends.

The polymeric film may be comprised of any thermoplastic polymer. Exemplary thermoplastic polymers include, but are not limited to, polymers selected from the group consisting of polymethyl methacrylate (PMMA), polycarbonate (PC), polyvinylacetate (PVAc), polystyrene (PS), polypropylene, polyethylene, polystyrene, polymethyl methacrylate, poly(amides), poly(butylene), poly(pentadiene), polyvinyl chloride, polycarbonate, polybutylene terephthalate, polysulfone, polyimide, cellulose, cellulose acetate, ethylene-propylene copolymer, ethylene-butene-propylene terpolymer, polyoxazoline, polyethylene oxide, polypropylene oxide, polyvinylpyrrolidone, and combinations thereof; an elastomer, polymer blend and copolymer selected from the group consisting of poly-dimethylsiloxane (PDMS), poly(isoprene), poly(butadiene), and combinations thereof.

BRIEF DESCRIPTION OF DRAWINGS

The accompanying drawings illustrate a disclosed embodiment and serve to explain the principles of the disclosed embodiment. It is to be understood, however, that the drawings are designed for purposes of illustration only, and not as a definition of the limits of the invention.

FIG. 1A shows a schematic partial cross-sectional view of a mold that can be used in the process of FIG. 1.

FIG. 3 shows an optical microscopy image of a mold used in the disclosed duo-mold method having a formed T-bar polymeric structure residing therein. The scale of FIG. 3 is 20 µm.

DETAILED DISCLOSURE OF EXEMPLARY EMBODIMENT

A non-limiting example of the invention, and a comparative example, will be further described in greater detail by reference to specific Examples, which should not be construed as in any way limiting the scope of the invention.

Figure 1:
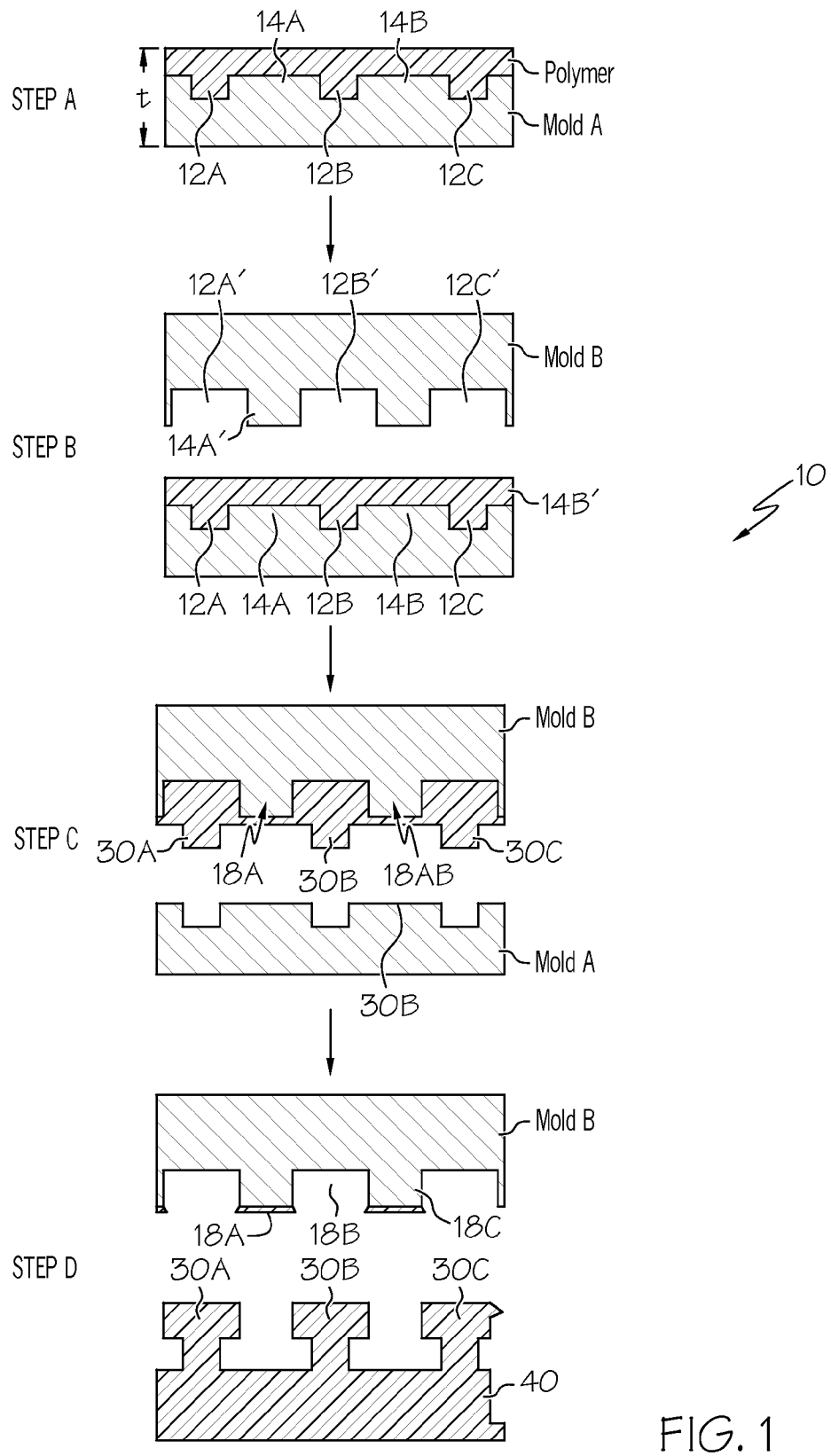
FIG. 1 schematically illustrates a disclosed duo-mold imprinting processes of a disclosed embodiment.

Referring to FIG. 1 there is disclosed a schematic illustration of a disclosed duo-mold imprinting processes 10. In step (A), there is disclosed the step of spin-coating a polymer onto the mold pattern surface of a first mold ("Mold A"). The mold A surface defines a pattern consisting of trenches (12A,12B, 12C), which extend along the length of the mold A. Between the trench pair (12A,12B) and trench pair (12B,12C) are respectively disposed projections (14A,14B).

The patterned silicon (Si) Mold A has been treated with a low surface energy silane (1 mM perfluorodecyltrichlorosilane (FDTS) solution in heptane). The surface treatment is performed in a nitrogen/inert gas glove box or in an environment where the relative humidity of the atmosphere is low (<20% RH). The silanes are dissolved in an anhydrous organic solvent such as n-heptane to a concentration of 1 mM. The silicon mold, oxygen plasma cleaned, is immersed in the silane solution for 10 minutes. On completion of the treatment, the mold is rinsed with n-heptane and blow dried with dry nitrogen gas.

A polymer solution, for example a poly(methyl methacrylate) (PMMA) in toluene, is then spin-coated onto the silane-treated mold A such that it fills up the trenches and forms a thin film. The choice of surface treatment and the polymers are interrelated, and judicious selection is needed in order to obtain a contiguous film. For example, when the combination of FDTS (for surface treatment) and PMMA (spin-coated polymer) are used, PMMA dissolved in toluene or propylene glycol methyl ether acetate (PGMEA) will give a uniform coating. The molds described herein may be fabricated by a variety of techniques including, but not limited to, photolithography, holographic lithography, e-beam lithography, ion-beam lithography, and combinations thereof.

It is important to note that the thickness (t) of the initial polymer film layer must be carefully selected to ensure that a frangible portion (hereafter called the "residue layer") forms and is capable of breaking when the formed polymeric structure is imprinted on a substrate as will be described further below.

Figure 2A:
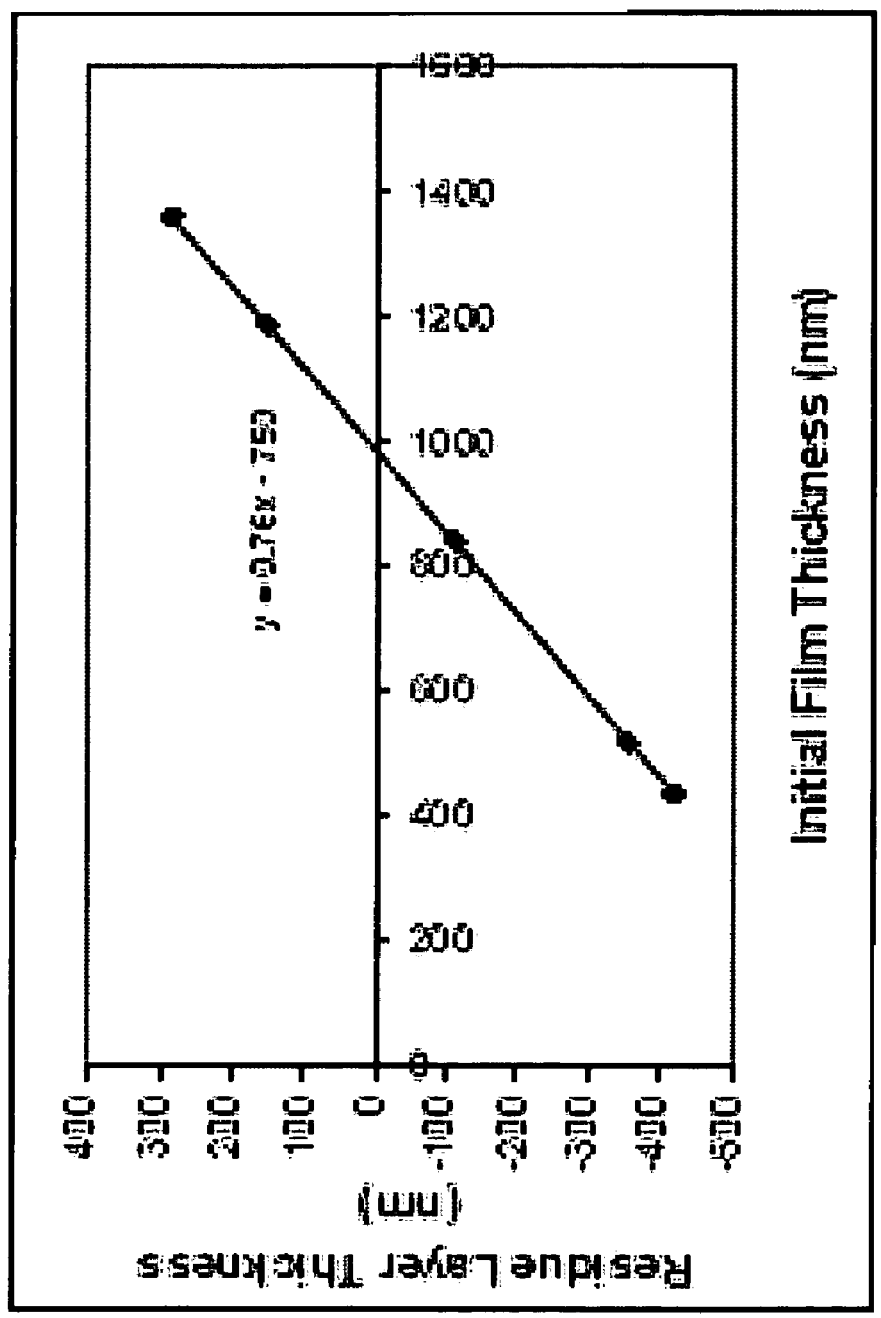
FIGS. 2A and B depict: 2(A) a graph showing the predicted residual layer thickness of a formed T-bar polymeric structure made according to a disclosed embodiment versus the initial polymer film coating layer of PMMA having a molecular weight of 15000, which is applied to a mold; and 2(B) a graph showing the predicted residual layer thickness of a formed T-bar polymeric structure made according to a disclosed embodiment versus concentration of PMMA having a molecular weight of 15000, which is applied to a mold.

One method of controlling the residual layer thickness is by controlling the initial polymer film thickness (t), which may be determined from the graph and equation found in FIG. 2A for PMAA having a molecular weight of 15000. This figure shows the predicted residual layer thickness of a formed T-bar polymeric structure versus the initial film thickness of PMMA.

The data of FIG. 2A determines the residue layer thickness for a given initial film thickness. The data points used to generate the linear regression of FIG. 2A have been experimentally verified to predict the initial film thicknesses with a modeled calculation applied to predict the residue layer thickness. Setting y=0 will yield the desired initial film thickness for residue layer self-removal. Negative values indicate inadequate trench filling.

The data of FIG. 2A was calculated by multiplying the experimentally determined initial film thickness by the free volume loss (~24% of the total polymer volume is lost during the imprinting process). From this value is subtracted the estimated film thickness (t) needed to completely fill the trenches (12,12b,12C) of a periodic grating mold A using formula (1):

$$t \approx \frac{d}{(1+b/a)} \quad (1)$$

As can be seen from FIG. 1A, the value "a" is the width of any particular trench in cross-section, assuming all trenches are geometrically the same; value "d" is the depth of the trench extending into said mold, assuming there is no variance in trench depth; and value "b" is the width of any particular protrusion in cross-section, assuming all protrusions are geometrically the same.

In this exemplary embodiment, a is 1 μm, d is 1 μm and b is 1 μm.

Making the residue layer extremely thin by setting the linear fit to the data equal to zero (i.e. setting y=0 as given in equation (1)) will maximize the self-removal of the residue layer and hence the process yield. Performing this calculation will yield a desired initial film thickness of ~990 nm. It has been found by the inventors that a very thin residue layer (ie <10 nm thick) is mechanically unstable and can be separated easily from the imprinted structures due to shear forces imposed when the formed polymeric structure is stamped on a substrate as will be described further below.

Figure 2B:
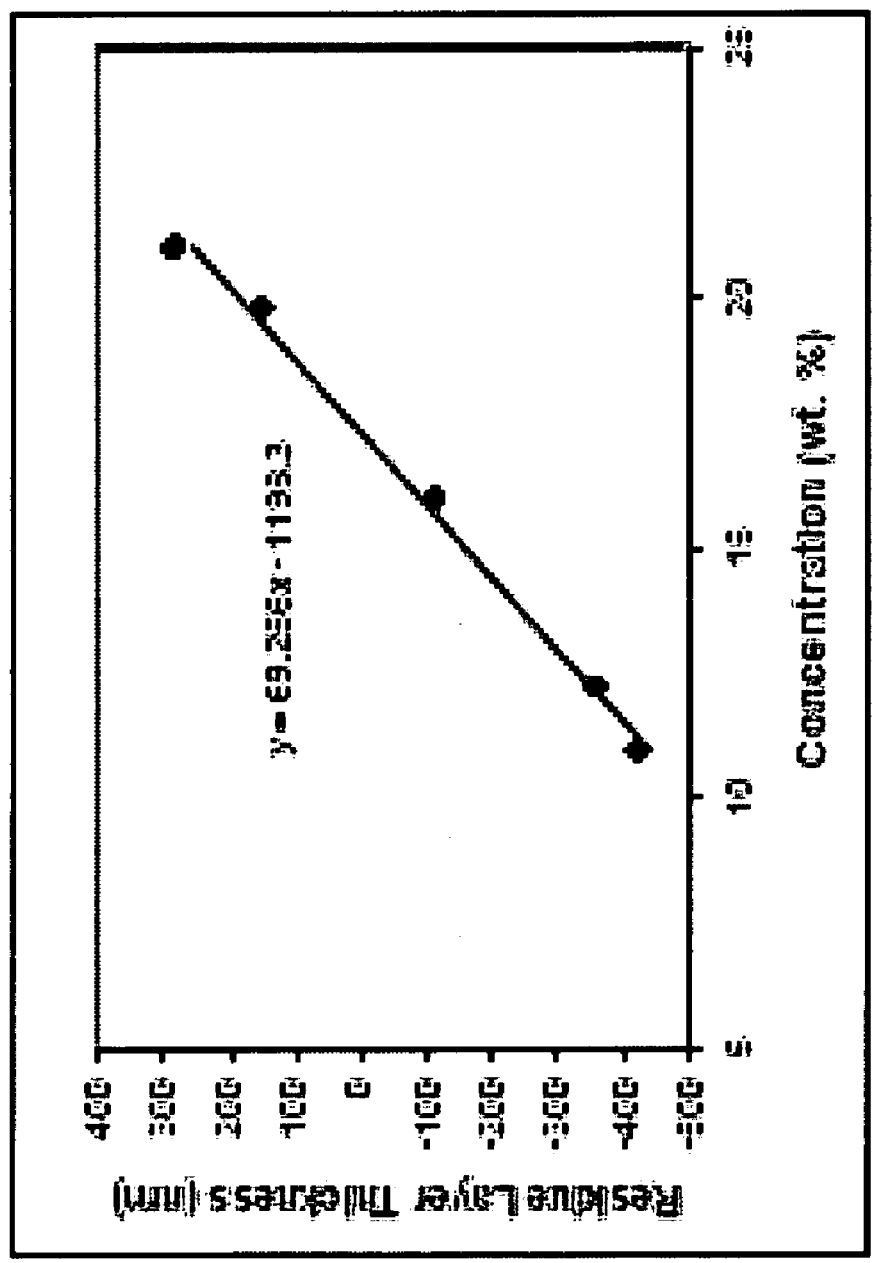

Referring to FIG. 2B there is shown a graph showing the predicted residual layer thickness of the formed T-bar polymeric structure versus the PMAA concentration in PMMA polymer film having a molecular weight of 15000. The regression line shown in FIG. 2A is the same regression as in FIG. 2B, but the units along the X-axis of FIG. 2B have been converted to concentration (in wt. %) to the thickness of the resulting spincast film in nm.

Following spin-coating of PMMA polymer in step A of FIG. 1, a second Si mold (mold B) is aligned above mold A. The mold B surface defines a pattern consisting of trenches (12A',12B',12C'), which extend along the length of the mold B and which, in step B of FIG. 1, are respectively disposed directly above corresponding trenches (12A,12B,12C) of mold A. Between the trench pair (12A',12B') of mold B and trench pair (12B',12C') of mold B are respectively disposed projections (14A',14B'). In this exemplary embodiment, the height of the projections (14A',14B') from the base of trenches (12A',12B',12C') is 1 μm while the width of each of the trenches (12A',12B',12C') is also 1 μm.

In step B of FIG. 1, projections (14A',14B') of mold B are respectively disposed directly above corresponding projections (14A',14B') of mold A.

The patterned silicon (Si) Mold B has been treated with a first low surface energy silane (1 mM phenethylmethyltrichlorosilane (PEDS) solution in heptane) followed by a second more concentrated silane solution (1 mM perfluorodecyltrichlorosilane (FDTS)). This results in a medium surface energy mold. Other silane solutions that could be used include octadecyltrichlorosilane (OTS) or octadecylmethyldichlorosilane (ODS). The purpose of the sequential surface treatment is to obtain a mold surface energy that is low in absolute terms but higher than mold A. Typically, the surface treatment is performed in a nitrogen/inert gas glove box or in an environment where the relative humidity of the atmosphere is low (<20% RH) The silanes are dissolved in an anhydrous organic solvent such as n-heptane to a concentration of 1 mM. The silicon mold, oxygen plasma cleaned, is immersed in the silane solution for 10 minutes. On completion of the treatment, the mold is rinsed with n-heptane and blow dried with dry nitrogen gas. A second treatment with another 1 mM silane solution for 10 minutes is carried out for molds that require a sequential silane treatment. On completion of the second treatment, the mold is rinsed with n-heptane and blow dried with dry nitrogen gas.

In step C of FIG. 1, mold B is pressed at a suitable pressure onto the polymer-coated mold A at a temperature above the glass transition temperature ($T_g$) of the polymer. The projections (14A',14B') of mold B respectively press into and against the projections (14A,14B) of mold A, while the polymer coating above trenches (12A',12B',12C') is accommodated therein.

Referring further to step (C), mold B is then separated below the $T_g$ of the polymer, thus forming three 3-D structures (30A,30B,30C) that are T-bar shaped when viewed in cross section. The T-bar structures (30A,30B,30C) are transferred from mold A to mold B. This transfer is made possible by the difference in surface energies of the two molds. Since mold B has a surface energy higher than the surface energy of mold A, the polymer film preferentially adheres to mold B and thus results in the transfer of the polymer film.

It will be appreciated that in step A, due to the controlled thickness of the initial polymer film that has been spincast on mold A, the indentation depth of mold B during the imprinting step will be such that the residual layer that forms between the protrusions of mold A and the protrusions of mold B will be extremely thin, thus forming respective frangible portions (18A,18B) (as shown in step (c)) as the projections (14A', 14B') of mold B are pressed therein. These frangible portions (18A,18B) have a thickness less than 10 nm and are capable of breaking as will be described further below.

Referring now to step (d), the mold B having the formed T-bar structures (30A,30B,30C) connected by frangible portions (18A,18B) residing therein, are aligned above an oxygen plasma treated silicon substrate 40. The plasma treatment of the silicon substrate 40 imparts it with a high surface energy (ie >50 mJ/m$^2$).

The mold B is pressed onto the substrate 40 at a relatively low pressure (ie <20 Bars (2 MPa)) and at a temperature below the glass transition temperature ($T_g$) (ie <80° C.). The projections (14A',14B') of mold B apply a shear force to the frangible portions (18A,18B), causing them to break and thereby separate from the T-bar structures (30A,30B,30C). However, as the frangible portions (18A,18B) are not in contact with the substrate and due to the medium surface energy of the mold B, the frangible portions (18A,18B) remain adhered to mold B.

As the substrate 40 has a relatively high surface energy that is higher than mold B, the compressive pressure force causes the T-bar structures (30A,30B,30C) to adhere to the substrate 40.

Accordingly, it is during this mold-substrate stamping step (d) that the frangible portions (18A,18B) self-remove to leave the final, isolated T-bar column structures (30A,30B,30C) on the substrate 40. Since the patterned film remains contiguous until the final imprinting step (d), the thin residue frangible portions (18A,18B) must shear off and remain attached to mold B as shown in FIG. 1. And because the frangible portions (18A,18B) are suspended above the substrate 40 and never make contact with it, it is not transferred to the substrate 40. Hence, it is possible to form the T-bar column structures (30A,30B,30C) without having to remove the polymer residual layer such as by an RIE step.

It will be appreciated that the selection of the silane treatments enable the transfer of the polymer film from one Si mold to another, and serve to facilitate the final release from the mold to form either supported or free-standing 3-D structures. Such selectively-applied silane treatments provide for the differential surface energies. Surface energy manipulation is a simple and convenient way of determining which surface the patterned polymer film will adhere to. In using such surface energy manipulation, it is generally assumed that the surface areas in contact with the patterned polymer film are similar. To more accurately determine which surface the patterned polymer film will adhere to, the work of adhesion per unit area (or work of separation per unit area) between the polymer and the surface should be calculated. The amount of work needed to separate is obtained by multiplying the surface area of the mold by the work of adhesion per unit area. The patterned polymer film will remain on the mold with the larger work required to separate.

EXAMPLE 1

Fabrication of T-Bar Structure:PMMA

Step A: A 17.3% wt. PMMA (Average Mw ~15000) in toluene solution was spun coated at 3000 rpm for 30 seconds onto mold A to obtain a 990 nm thick film, ±30 nm. Mold A with the PMMA coating was then baked at 150° C. for 5 minutes to remove any remaining solvent in the film.

The features on Mold B are aligned with that on mold A using precision alignment tools. Mold B is then brought into contact with the PMMA-coated Mold A after the alignment step.

Step C: Mold B is pressed into the PMMA-coated Mold A at a pressure of 50 Bars (5 MPa) at 150° C. for 5 minutes. After imprinting, the 990 nm thick film formed in step A is reduced to a thickness of less than 10 nm on the frangible portions (18A,18B). After the imprinting, the molds were cooled down to 65° C. and separated resulting in transfer of the patterned PMMA film from mold A to mold B.

Referring to FIG. 3, there is shown an optical microscopic image of mold A having the formed T-bar polymeric structure (35) residing therein. The scale of FIG. 3 is 20 µm. Although typically most of the T-bar structures (35) transfer from mold A to mold B, there is not always uniform transfer and some of the T-bar structures remain on mold A as shown by FIG. 3. It can be seen in FIG. 3 that the areas (37) between the PMMA T-bar structures is consistent with bare silicon (i.e. there is no residue layer present). Ideally, when the transfer yield is 100%, mold A is completely clear of any PMMA film. However, due to inefficient transfer (ie perhaps due to uneven surface energy treatment of the molds) a selected area of mold A shows that some PMMA structures remain after step C but the frangible portions still break off and adhere to mold B. Hence, FIG. 3 shows the contrast between bare silicon and a PMMA film in the microscope image and demonstrates that even in situations where the T-bar structures remain on mold A (due to non-uniformity of the transfer), the residue layer will still be transferred to mold B. FIG. 3 also demonstrates evidence that the residue layer is sufficiently thin such that it can be sheared off and separated from the T-bar structures very easily, even during step C.

Figure 4:
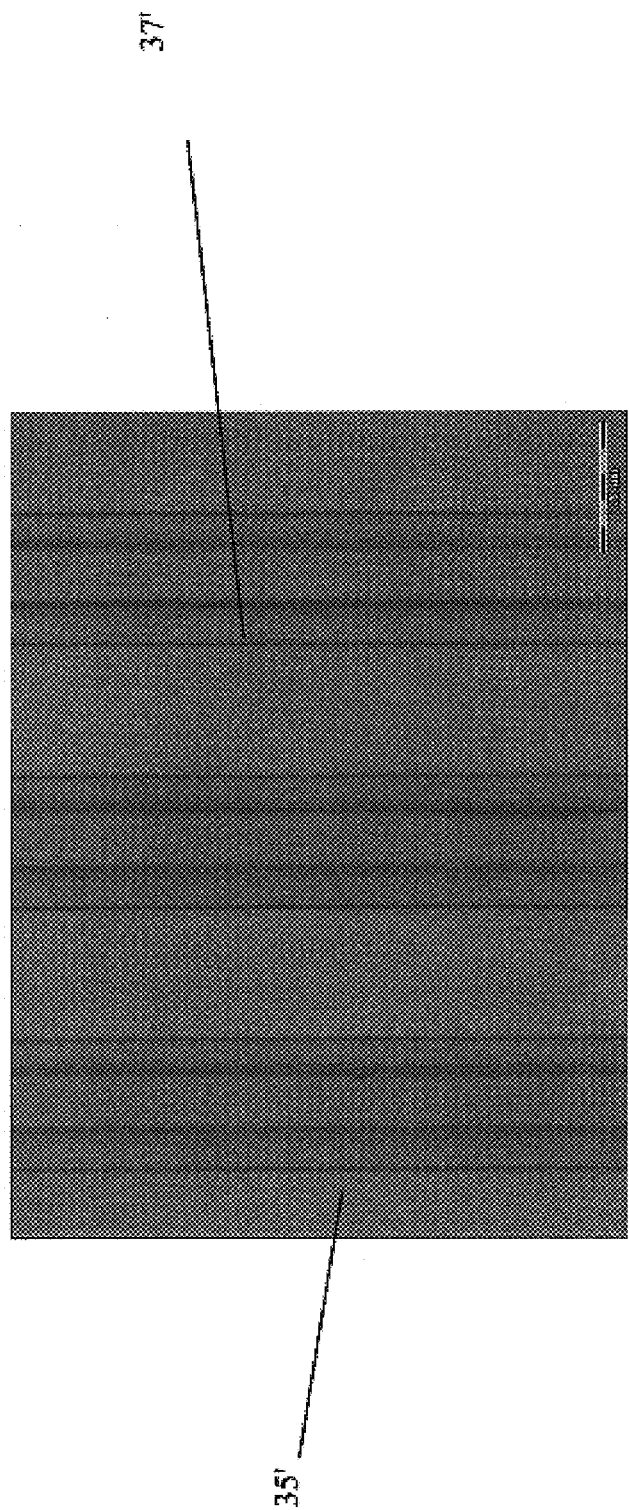
FIG. 4 shows an optical microscopy image of the other mold used in the disclosed duo-mold method, which shows the presence of residue residing thereon. The scale of FIG. 4 is 20 µm.

Referring to FIG. 4, there is shown an optical microscopic image of mold B directly after step C. The scale of FIG. 4 is 20 µm. The T-bar structures (35') and the connecting frangible portions (residue layer) (37') can be clearly seen. Hence, FIG. 4 demonstrates that when the surface energy contrast between mold A and mold B is sufficiently higher than the entire polymer film (ie T-bar structures and residue layer), the polymer film is transferred to mold B. Furthermore, FIG. 4 demonstrates that the residue layer is clearly present and always transfers to mold B.

Step D: For the fabrication of T-bar structures, the PMMA-coated mold B was then pressed onto an oxygen plasma cleaned silicon substrate at a temperature of 50° C. and pressure of 15 Bar (1.5 MPa) for 5 minutes before cooling to 50° C. where mold B was separated from the substrate 40.

Application of pressure by mold B against the substrate 40 caused the frangible portions (residue layer) to shear and thereby break away from the T-bar structures. Hence, the T-bar structures adhere to the substrate 40 having a high surface energy while the frangible portions (residue layer) don't contact the substrate but remain attached to mold B after shearing from the T-bar structures.

Figure 5:
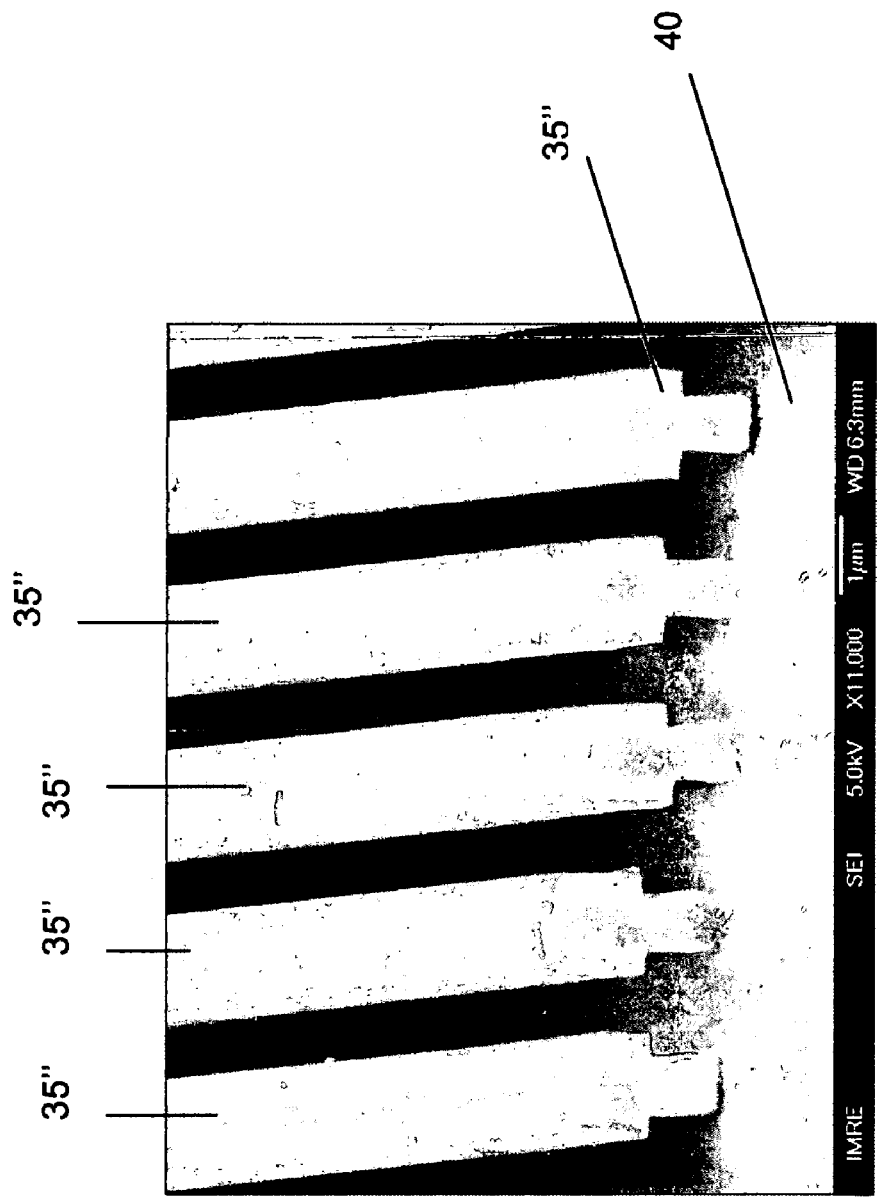
FIG. 5 shows an SEM cross-section of a column of T-bar shaped polymeric nanostructures fabricated using the disclosed method at a magnification of 11,000.

The T-bar structures made in this method are shown in FIG. 5, which shows an SEM micrograph of the imprinted T-bar structures (35") supported on the silicon substrate 40. In this case, the area of the crossbar of the T is 1 μm², while the strut of the T is approximately 1 μm high and 500 nm wide. The period spacing between each column is 2 μm. It can be seen in FIG. 5 that no residue layer is present on the substrate 40 and hence, there is no need to conduct RIE on the T-bar structures mounted on the substrate. It can be clearly seen from FIG. 5 that the formed T-bar structures have a smooth profile and vertical side walls as they have not been exposed to RIE such as with oxygen plasma.

EXAMPLE 2

Fabrication of "Stair-Step" Structure

Steps A to C were repeated as for Example 1 described above, however in this example, during step (D) the temperature and pressure were increased to 65° C. and 20 Bar (2 MPa).

Figure 6:
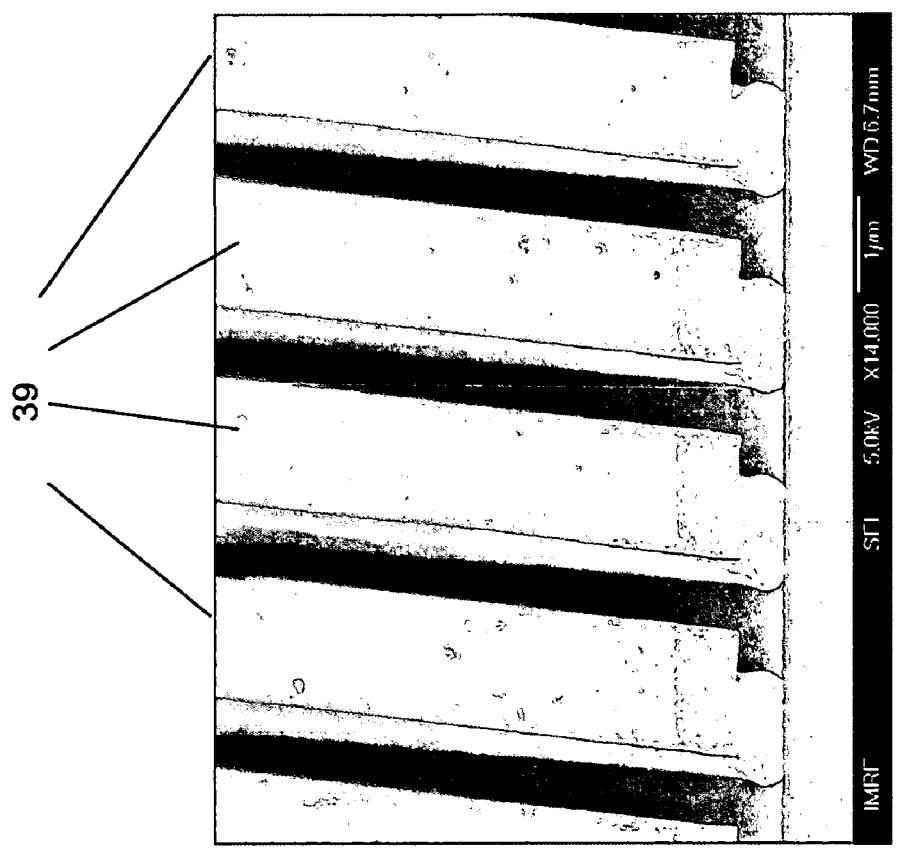
FIG. 6 shows an SEM cross-section of a column of "stair step" shaped polymeric nanostructures fabricated using the disclosed method.

FIG. 6 shows an SEM micrograph of imprinted "stair step" structures (39) potentially useful for MEMS applications. The total height of each structure is ~1.25 um, with each individual "stair step" being ~1 um in width. The difference in shape from Example 1 was obtained due to the slightly raised temperature and pressure that were utilized in Example 2. During the stamping step (D), the polymer patterns that are in contact with the substrate deform as the glass transition temperature is approached because these structures are not confined by the mold. The back side of the patterned polymer film which is still attached to the mold is still confined by the mold and cannot be deformed.

Without being bound by theory, it is thought that the deformation temperature is dependent on the molecular weight of the polymer. It has been found by the inventors that if polymer deformations are allowed to occur through manipulation of temperature and pressure during step (D), different types of structures can be formed from the same combination of molds. In example 2, the same steps were repeated except for Step (D) and during step (B), the top and bottom molds were aligned slightly offset.

COMPARATIVE EXAMPLE 3

Fabrication of T-Bar Structure Using RIE

Figure 7:
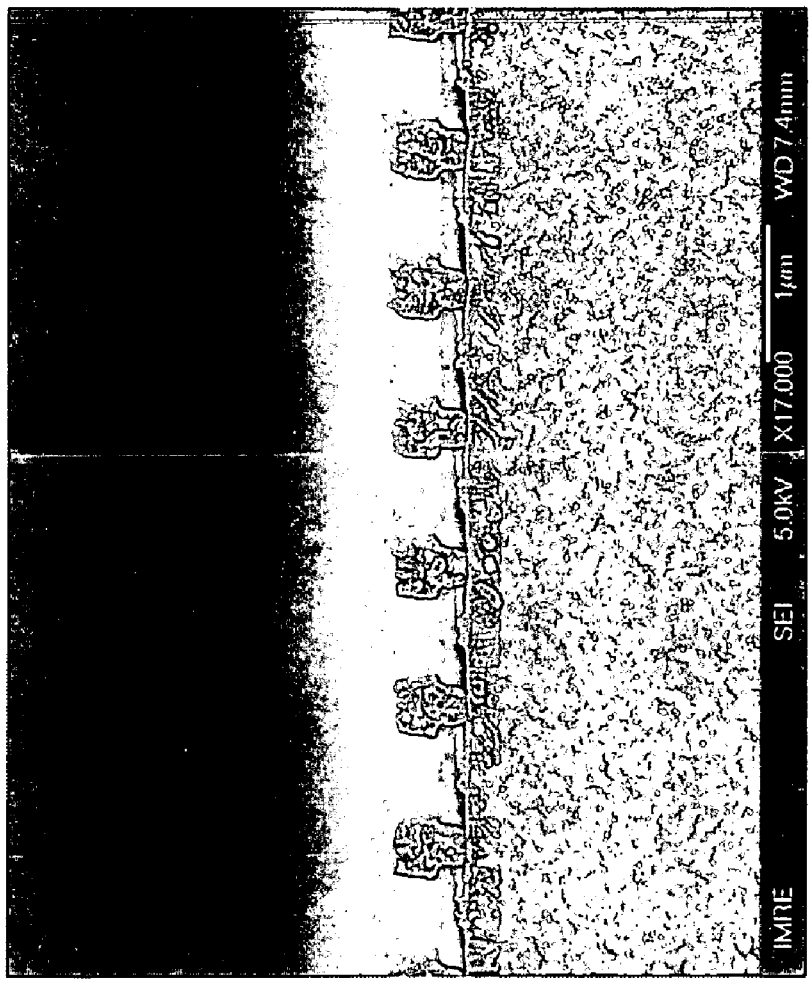
FIG. 7 shows an SEM cross-section of T-bar polymeric column nanostructures fabricated using conventional oxygen plasma RIE etch to remove residue layer and is therefore not made according the disclosed method.

Referring to FIG. 7, there is shown a T-bar array where the residue layer was removed with a ~200 mm oxygen plasma etch. The T-bar arrays of this example were made according to the method disclosed in US Patent Application No. 2005/0258571A1. The total height of the structures are ~600 nm. The width of the crossbar of each T-bar is ~350 nm, while the width of the strut of each T-bar is ~250 nm.

FIG. 7 provides an excellent comparison with the structures achieved in FIG. 5. Compared with 5, the structures of FIG. 7 have a very rough top surface and reduced crossbar overhang due to etch isotropy. Accordingly, although the structures of FIG. 7 were fabricated on a different scale to FIG. 5, it is still easy to see the benefits of avoiding an oxygen plasma etch step to remove the residue layer. The structures presented in FIG. 5 are obviously much smoother and cleaner, with vertical sidewalls and well-controlled dimensions compared to the T-bar structures of FIG. 7.

EXAMPLE 4

Fabrication of T-Bar Structure

Polystyrene

A styrene based polymeric resin was prepared which consisted of:

82 molar % styrene monomer (99% purity from Fluka and Riedel-de Haën, Switzerland);

26 molar % divinylbenzene as cross-linker (80% mixture of isomers from Sigma-Aldrich of United States of America); and 2 molar % benzyl peroxide as thermal initiator (Sigma-Aldrich of United States of America)

The styrene based polymeric resin was mixed for 6 hours before being filtered through a 0.2 μm filter.

The resin film was applied to mold A using a 1 mL syringe with a needle. The total volume was estimated to be 5-7 μL. The volume of the applied resin affects the thickness of the residual layer. A 0.1-2 μL adjustable volume pipette can be used to control the volume of applied resin film on mold A.

The steps A to D as described above for experiment 1 above were then repeated with the following exceptions:

Step A: 30° C. temperature, 20 Bar (2 MPa) pressure for 10 minutes to allow even spreading across the surface of mold A. The temperature was then raised to 110° C. and the pressure to 50 Bar (5 MPa) for 5 minutes in order to cure the resin and form polystyrene (PS) polymer film.

Figure 8:
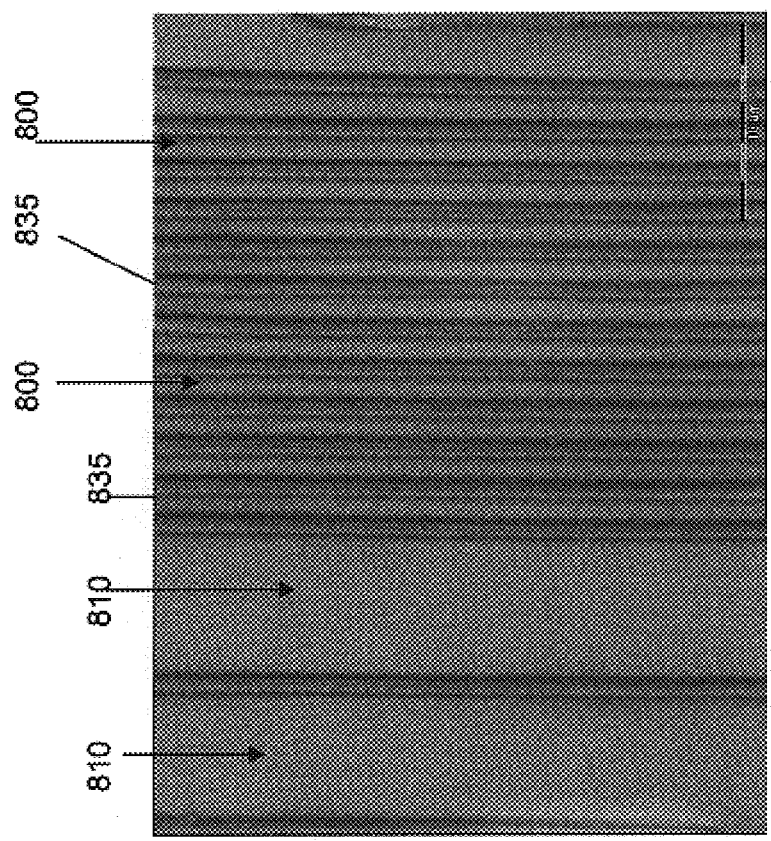
FIG. 8 shows an optical microscopy image at 1500 times magnification of a mold having formed T-bar structures, made in one disclosed example, residing thereon.
Figure 9:
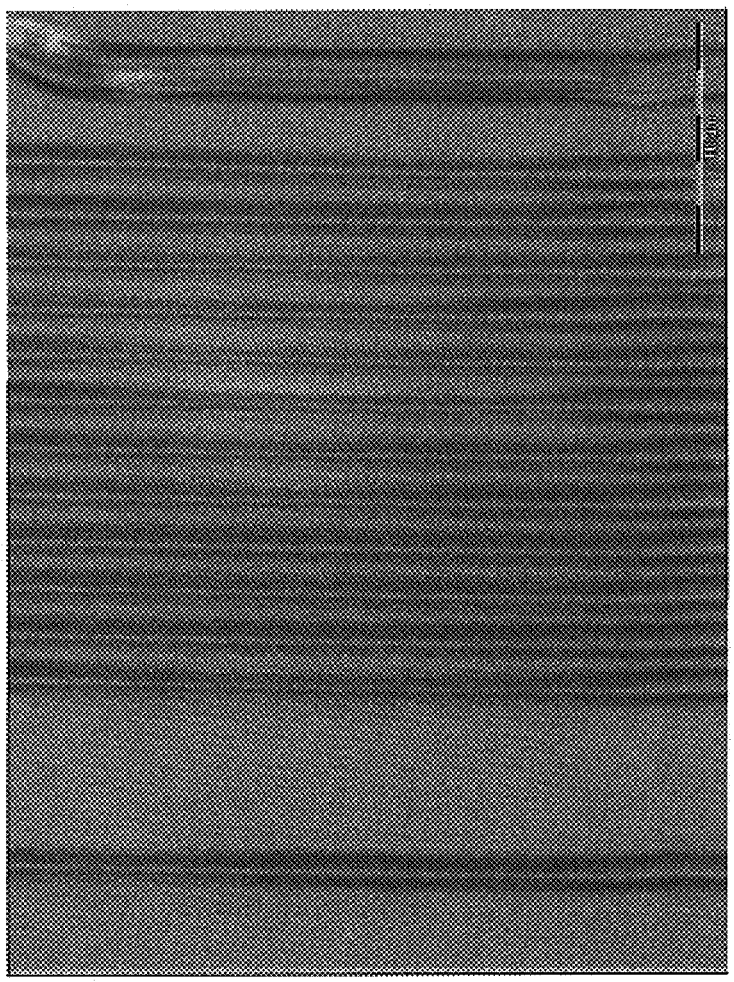
FIG. 9 shows an optical microscopy image of FIG. 8 at 1500 times magnification.

Step D: the stamping step was undertaken at 150° C. and the pressure to 50 Bar (5 MPa) for 5 minutes on an ITO substrate The de-molding step (C) resulted in nearly 100% of the cross-linked polymer film being transferred to mold B. Referring to FIG. 8, there is shown PS 1 μm wide T-bar structures completely adhered to the ITO substrate, without any residual layer disposed between the structures. The magnification of this image is 150×. The strip of T-bar structures 835 shown in FIG. 8, show the 1 μm wide crossbars of the T-bar structures. The T-bar struts are not shown due to the depth-of-field limitations of the microscope at this magnification. It can be seen from FIG. 8 that the grey-scale shading of the area between the polymer T-bars (ie refer to arrow 800) is the same as the bare substrate on the left side of the image and as shown by arrows 810. Referring to FIG. 9, there is shown an image of the strip shown in FIG. 8, except the image has been refocused to show the 500 nm wide struts of the T-bar columns. The struts were measured using the scale bar shown in the image and the width of these struts was confirmed to be ~500 nm. Hence, as observed, and as confirmed in FIG. 9, the disclosed method resulted in no residue layer spanning the area between the T-bar column structures.

EXAMPLE 5

Fabrication of Inverted Bar Structure

Polystyrene

The styrene based polymeric resin of Example 4 was used in this example and was filtered through a 0.2 μm filter before being applied to a 3:1 duty cycle mold (1.5 μm protrusion, 500 nm trench) pre-treated with 2 μM FDTS.

A flat surfaced silicon wafer chip was treated sequentially with 2 µM PEDS followed by FDTS treatment to give a slightly higher surface energy relative to the mold.

The resin film was applied to the mold using a 1 mL syringe with a needle.

Once the mold had been coated with the resin, the temperature was raised to 110° C. and the pressure to 40 Bar (4 MPa) for 5 minutes in order to cure the resin and form a polystyrene (PS) polymer film having a very thin film residual layer (frangible region). The short imprinting time prevented the PS from fully crosslinking, rendering it flexible enough to conform to the substrate for the stamping step.

A demolding step was undertaken in which the polymer coated mold was pressed against the treated silicon wafer chip to transfer the PS polymer film thereon. Demolding resulted in the transfer of 90-95% of the crosslinked polymer film to the treated silicon wafer. Some material remained on the FDTS 3:1 duty cycle mold, most likely from defects in the film reducing adhesion to the PEDS-FDTS substrate.

The stamping step was conducted at 180° C. and 40 bars (4 MPa) for 5 minutes onto an oxygen plasma treated ITO substrate. The high temperature caused complete crosslinking of the PS.

It was observed that the thin residual layer on the silicon wafer fractured and self-removed from the imprinted structures after release of the silicon wafer from the ITO substrate. This was due to a shear stress build-up which occurred where the imprinted feature meet the adjoining residual layer region because the imprinted features tended to remain attached to the ITO substrate due to its higher surface energy. The thin residual layer tended to remain attached to the silicon wafer, having never made contact with the substrate. Since the silicon wafer has no recessed features, the residual layer fracture did not occur during the stamping step.

Figure 10:
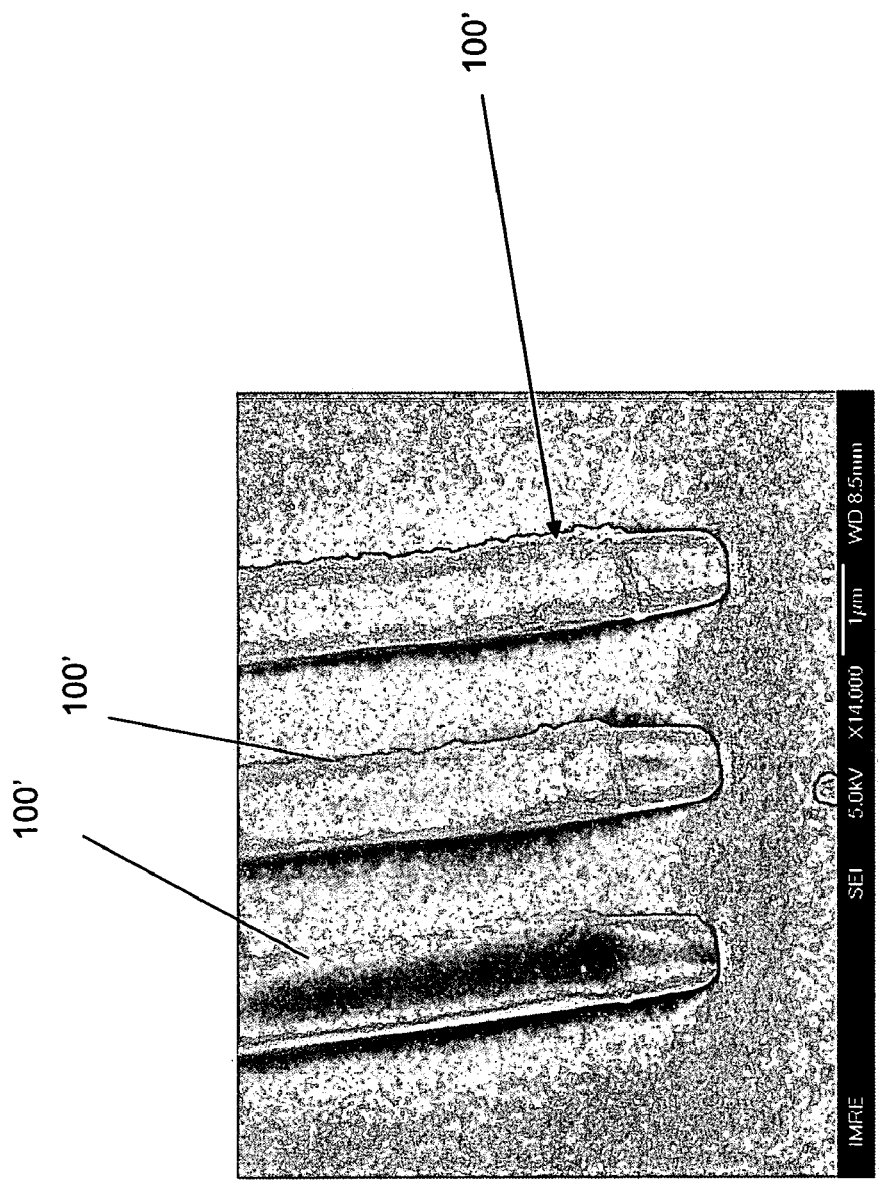
FIG. 10 shows an SEM image of bar structures made in accordance with one disclosed method at a magnification of 14000.

Referring to FIG. 10, there is shown an SEM image of the structures produced in this example at a magnification of 14000. The self-removal of the residual layer (frangible portions) from the polymer is evident by the jagged fracture line (100') shown in the SEM image. The observed jagged fracture line (100') is most likely due to the brittle nature of the PS, as compared to the more ductile PMMA.

These inversely tapered column structures are roughly 500 nm in width and come directly from the 3:1, 2 µm period, FDTS treated mold. In this example, the crossbar needed to make a "T" shaped structure is not present because the silicon wafer is flat. Hence, FIG. 10 further demonstrates the self-removal of the residual layer after separation of the silicon wafer from the ITO substrate

APPLICATIONS

An advantage of the presently disclosed methods is that it is not necessary to use reactive ion etching (RIE), or any other material removal step, to remove residue from the substrate. Accordingly, prior art problems associated with RIE techniques, such as oxygen gas-plasma etching, are avoided.

Advantageously, the disclosed method can be implemented to produce micro-sized and nano-sized structures having relatively straight or vertical sidewalls. Furthermore, the edges of the structures is relatively smooth compared to those subjected to an RIE technique.

Advantageously, the disclosed method can be used to maintain the chemical properties of the produced particle surfaces. Hence, problems, such as oxidation, when an oxygen plasma is used are avoided.

Advantageously, the disclosed methods provide for a direct patterning method that does not require a sacrificial layer/component. This allows for fewer processing steps.

Advantageously, the disclosed methods provide for patterning of well-defined 3-D structures with nano-scale dimensions, wherein such 3-D structures can be transferred to a substrate, or lifted-off as a free standing film or as individual 3-D structures.

Advantageously, the disclosed methods provide for a variety of 3-D micro- and/or nano-structures that can be imprinted, stacked, and/or assembled.

Advantageously, because the disclosed methods require little to no post-processing steps, the critical dimensions of the polymeric structures are maintained.

The present invention finds potential application in the areas of MEMS and NEMS devices (fluidics, actuators, lenses, resonators), sensors, integrated chip devices, photonic band gap structures (waveguides), and in drug/chemical delivery systems. This diversity of potential applications attests to the significance of the methods and processes of the present invention.

It will be apparent that various other modifications and adaptations of the invention will be apparent to the person skilled in the art after reading the foregoing disclosure without departing from the spirit and scope of the invention and it is intended that all such modifications and adaptations come within the scope of the appended claims.

The invention claimed is:

1. A method of making a three-dimensional (3-D) polymeric structure comprising the steps of:
    (a) forming a polymer film having a selected thickness on a structured surface of a first mold, said polymer film having a first side in contact with said structured surface, a second side opposite to said first side, and a glass transition temperature Tg;
    (b) pressing, at a temperature above Tg, the second side of the polymer film and a structured surface of a second mold relatively toward each other to form a 3-D structured polymer film therebetween and wherein said selected thickness of said polymer film forms at least one frangible portion thereon, said structured surfaces of the first and second molds having dissimilar surface energies to each other;
    (c) separating one of the first or second molds from the polymer film, at a temperature below Tg, to attach the 3-D structured polymer film to the mold having a higher surface energy relative to the other mold;
    (d) pressing said attached 3-D structured polymer film and a substrate relatively toward each other to attach said 3-D structured polymer film to said substrate, said substrate having a higher surface energy relative to the surface energy of the structured surface; and
    (e) separating said mold from said 3-D structured polymer film, wherein after said separating, said at least one frangible portion remains substantially attached to said mold while the remainder of said polymer film remains substantially attached to said substrate to form a 3-D polymeric structure thereon.

2. The method as recited in claim 1 further comprising: providing a polymer resist that is cross-linkable and cures.

3. A method for making a polymeric structure, the method comprising:
    coating a surface of a first and a second mold with different anti-stick coatings with differing surface energies;

spin-coating a polymer onto said surface of said first mold, wherein said surface of said first mold comprises a plurality of projections extending along a length of said first mold;

aligning said second mold above said first mold, wherein a surface of said second mold comprises a plurality of projections extending along a length of said second mold, wherein said plurality of projections of said second mold are disposed directly above corresponding projections of said plurality of projections of said first mold;

pressing said second mold onto said polymer-coated first mold at a temperature above a glass transition temperature of said polymer;

forming frangible portions in said polymer as said plurality of projections of said second mold are pressed into said plurality of projections of said first mold;

separating said second mold from said first mold below said glass transition temperature of said polymer forming three-dimensional structures that are T-bar shaped;

transferring said T-bar shaped structures to one of said first and said second mold with a higher surface energy due to a difference in surface energies of said first mold and said second mold;

aligning said T-bar structures and said frangible portions of said polymer film attached to one of said first and said second mold with said higher surface energy above a treated substrate; and pressing one of said first and said second mold with said higher surface energy with said attached polymer film onto said substrate at a temperature below said glass transition temperature of said polymer, wherein said projections of one of said first and said second mold with said higher surface energy apply a shear force to said frangible portions thereby causing said frangible portions to break, wherein said frangible portions remain adhered to one of said first and said second mold with said higher surface energy, wherein said T-bar structures separate from one of said first and said second mold with said higher surface energy and adhere to said substrate due to a compressive pressure force from pressing one of said first and said second mold with said higher surface energy onto said substrate as well as due to said substrate comprising a higher surface energy than said surface energy of one of said first and said second mold with said higher surface energy.

4. The method as recited in claim 3, wherein said surface of said first mold comprises one of cavities, projections and combinations of cavities and projections.

5. The method as recited in claim 3, wherein said first mold comprises a silicon mold.

6. The method as recited in claim 3, wherein said first mold is coated with an anti-stick coating comprising Teflon™.

7. The method as recited in claim 3, wherein said first mold is treated with a silane anti-stick coating.

8. The method as recited in claim 7, wherein said silane anti-stick coating comprises perfluorodecyltrichlorosilane.

9. The method as recited in claim 7 further comprising:
spin-coating said polymer onto said silane-treated first mold such that it fills up said plurality of projections of said first mold and forms a thin film.

10. The method as recited in claim 3, wherein said polymer comprises one of the following: polymethyl methacrylate, polycarbonate, polyvinylacetate, polystyrene, polypropylene, polyethylene, polystyrene, polymethyl methacrylate, poly(amides), poly(butylene), poly(pentadiene), polyvinyl chloride, polycarbonate, polybutylene terephthalate, polysulfone, polyimide, cellulose, cellulose acetate, ethylene-propylene copolymer, ethylene-butene-propylene terpolymer, polyoxazoline, polyethylene oxide, polypropylene oxide, polyvinylpyrrolidone, and combinations thereof.

11. The method as recited in claim 3, wherein said polymer comprises a cross-linkable polymer resist material.

12. The method as recited in claim 3, wherein said second mold comprises a silicon mold.

13. The method as recited in claim 3, wherein said surface of said second mold comprises one of cavities, projections and combinations of cavities and projections.

14. The method as recited in claim 3, wherein a height of one of said disposed projections of said second mold is about 1 micrometer, wherein a width of each of said plurality of projections of said second mold is about 1 micrometer.

15. The method as recited in claim 3, wherein a width of each of said plurality of projections of said second mold is between 250 nanometers to 20 micrometers.

16. The method as recited in claim 3, wherein a width of each of said plurality of projections of said second mold is between 20 nanometers to 200 micrometers.

17. The method as recited in claim 3, wherein a height of one of said disposed projections of said second mold is between 250 nanometers to 2 micrometers.

18. The method as recited in claim 3, wherein a height of one of said disposed projections of said second mold is between 20 nanometers and 10 micrometers.

19. The method as recited in claim 3, wherein said surface of said second mold comprises cavities, wherein said cavities of said second mold are disposed directly above corresponding disposed cavities of said first mold.

20. The method as recited in claim 3, wherein a combination of silane anti-stick coatings are deposited on said second mold, wherein said combination of silane anti-stick coatings comprise phenethylmethyldichlorosilane and perfluorodecyltrichlorosilane.

21. The method as recited in claim 3, wherein a surface energy of said second mold is higher than a surface energy of said first mold.

22. The method as recited in claim 3, wherein said frangible portions have a thickness of 10 nanometers or less.

23. The method as recited in claim 3, wherein said substrate has a surface energy exceeding 50 mJ/m$^2$.

24. The method as recited in claim 3, wherein an amount of pressure used in pressing one of said first and said second mold with said higher surface energy onto said substrate is less than 2 MPa.

25. The method as recited in claim 3, wherein said substrate comprises one of the following: glass, fused silica, quartz, oxide, silicon carbide, and III-V compound.

26. The method as recited in claim 3, wherein said substrate is coated with one of the following: glass, fused silica, quartz, oxide, silicon carbide, and III-V compound.

27. The method as recited in claim 3, wherein said first mold comprises one of the following: silicon, glass, fused silica, quartz, metal oxide, silicon carbide, carbon and polydimethylsiloxane.

28. The method as recited in claim 3, wherein said first mold is coated with one of the following: silicon, glass, fused silica, quartz, metal oxide, silicon carbide, carbon and polydimethylsiloxane.

29. The method as recited in claim 3, wherein said second mold comprises one of the following: silicon, glass, fused silica, quartz, metal oxide, silicon carbide, carbon and polydimethylsiloxane.

30. The method as recited in claim 3, wherein said second mold is coated with one of the following: silicon, glass, fused silica, quartz, metal oxide, silicon carbide, carbon and polydimethylsiloxane.

31. The method as recited in claim 3, wherein said substrate is treated with a partially ionized oxygen gas plasma.

32. The method as recited in claim 3, wherein said substrate is treated with a partially ionized gas plasma containing one or a combination of the following gasses: argon, nitrogen and oxygen.

33. The method as recited in claim 3 further comprising: applying an adhesion promoter to said substrate.

* * * * *